United States Patent
Chiang (10) Patent No.: US 10,945,943 B2
(45) Date of Patent: Mar. 16, 2021

(54) EXTRACT OF DRAGON FRUIT FLOWER, METHOD FOR PREPARING THE SAME, USE THEREOF, AND SKIN COMPLEXION IMPROVED COMPOSITION THEREOF

(71) Applicant: M.H. Biotechnology Corporation, Ltd., Douliou (TW)

(72) Inventor: Hsiang-Hsun Chiang, Douliou (TW)

(73) Assignee: M.H. Biotechnology Corporation, Ltd., Douliou (TW)

( * ) Notice: Subject to any disclaimer, the term of this patent is extended or adjusted under 35 U.S.C. 154(b) by 279 days.

(21) Appl. No.: 16/022,119

(22) Filed: Jun. 28, 2018

(65) Prior Publication Data

US 2019/0008756 A1    Jan. 10, 2019

(30) Foreign Application Priority Data

Jun. 30, 2017 (TW) .................................. 106122047

(51) Int. Cl.
| | | |
|---|---|---|
| *A61K 36/00* | (2006.01) | |
| *A61K 8/9789* | (2017.01) | |
| *A61Q 19/02* | (2006.01) | |
| *A61Q 19/00* | (2006.01) | |
| *A61Q 19/08* | (2006.01) | |
| *A61K 36/33* | (2006.01) | |
| *A61P 17/02* | (2006.01) | |

(52) U.S. Cl.
CPC ............ *A61K 8/9789* (2017.08); *A61K 36/33* (2013.01); *A61P 17/02* (2018.01); *A61Q 19/007* (2013.01); *A61Q 19/02* (2013.01); *A61Q 19/08* (2013.01); *A61K 2236/00* (2013.01)

(58) Field of Classification Search
None
See application file for complete search history.

(56) References Cited

FOREIGN PATENT DOCUMENTS

| CN | 103451065 A | * 12/2013 |
|---|---|---|
| CN | 104186860 A | * 12/2014 |

\* cited by examiner

*Primary Examiner* — Qiuwen Mi (74) *Attorney, Agent, or Firm* — Muncy, Geissler, Olds & Lowe, P.C.

(57) ABSTRACT

The present invention provides an extract of dragon fruit flower. The extract of dragon fruit flower is prepared by the following steps. A dragon fruit flower is provided. The dragon fruit flower is dried and then cut into pieces. An extraction process is provided, which includes a mixing step, a heating step, a cooling step, a reheating step, and an extracting step. In the mixing step, the pieces of the dragon fruit flower are mixed with an alcohol solution to obtain a mixture for processing the following steps. After finishing the extraction process, the mixture is separated into a solid part and a liquid part, wherein the liquid part includes the extract of the dragon fruit flower.

18 Claims, 10 Drawing Sheets

EXTRACT OF DRAGON FRUIT FLOWER, METHOD FOR PREPARING THE SAME, USE THEREOF, AND SKIN COMPLEXION IMPROVED COMPOSITION THEREOF

RELATED APPLICATIONS

This application claims priority to Taiwan Application Serial Number 106122047, filed Jun. 30, 2017, which is herein incorporated by reference.

BACKGROUND

Technical Field

The present disclosure relates to an extract of plant and a method for preparing the same. More particularly, the present disclosure relates to an extract of dragon fruit flower and a method for preparing the same.

Description of Related Art

Dragon fruit (or pitaya) is a fruit of a perennial plant of genus *Hylocereus* or genus *Selenicereus* of family Cactaceae. Dragon fruit has a variety of nutrients, anthocyanins and water-soluble dietary fibers, and has excellent effects to the health of human. In Taiwan, the abundance of dragon fruit is about June to October every year, and there is few diseases and pest damages happened during the abundant harvest period, thus the dragon fruit plant is one of the fruits which can be organically planted without pesticides.

Dragon fruit flower is similar to night-blooming *cereus* in appearance and flowering cycle. The Dragon fruit flower not only has a pleasant scent but also is rich in polysaccharides and flavonoids with antioxidant function, so that dragon fruit flower can be applied to both ornamental and eating applications. Dragon fruit plant blooms in every April to May and there are about seven to ten batches of flower buds in season. When one batch of flower buds blooms, another batch of flower buds will begin to generate and then bloom in sequence. Therefore, in order to ensure that dragon fruits can obtain sufficient nutrients, it is necessary to process several flower removing operations during the growing period of dragon fruits and leave an appropriate amount of flower buds so as to prevent the quality of dragon fruits from influences caused by an excessive number of fruits. However, the number of dragon fruit flower buds removed during the flower removing operation is very large. Except for a few of the dragon fruit flower buds are further used for food or other applications, the rest of the dragon fruit flower buds can only be processed as agricultural wastes. It not only wastes precious biological resources but also increases the complexity of the processing of agricultural waste.

Therefore, how to solve the problem of agricultural wastes generated during the flower removing operation as well as increase the additional economic benefits of dragon fruit has become a developmental goal of related industries.

SUMMARY

According to one aspect of the present disclosure, a method for preparing an extract of a dragon fruit flower includes the following steps. The dragon fruit flower is provided. The dragon fruit flower is dried, and then the dragon fruit flower is cut into chips after drying so as to obtain a plurality of dragon fruit flower pieces. An extraction process is performed, and the extraction process includes the following steps. A mixing step is provided, a heating step is provided, a cooling step is provided, a reheating step is provided and an extracting step is provided. In the mixing step, an alcohol solution is mixed with the dragon fruit flower pieces so as to form a mixture. In the heating step, the mixture is heated up to a heating temperature and then is reacted for a heating time. In the cooling step, the mixture is cooled down to a room temperature and then is rested for a cooling time. In the reheating step, the mixture is heated up to a reheating temperature and then is reacted for a reheating time. In the extracting step, the mixture is cooled down to the room temperature and then is stirred and reacted for an extracting time. Finally, a solid component is removed from the mixture so as to obtain an extract liquid, wherein the extract liquid includes the extract of the dragon fruit flower.

According to another aspect of the present disclosure, a method for enhancing antioxidant activity includes administering an effective amount of an extract of a dragon fruit flower, wherein the extract of the dragon fruit flower is prepared by the aforementioned method for preparing the extract of the dragon fruit flower.

According to further another aspect of the present disclosure, a method for enhancing wound healing includes administering an effective amount of an extract of a dragon fruit flower, wherein the extract of the dragon fruit flower is prepared by the aforementioned method for preparing the extract of the dragon fruit flower.

According to still another aspect of the present disclosure, a skin complexion improved composition includes an effective amount of an extract of a dragon fruit flower, wherein the extract of the dragon fruit flower is prepared by the aforementioned method for preparing the extract of the dragon fruit flower.

BRIEF DESCRIPTION OF THE DRAWINGS

The present disclosure can be more fully understood by reading the following detailed description of the embodiment, with reference made to the accompanying drawings as follows.

DETAILED DESCRIPTION

Method for Preparing an Extract of a Dragon Fruit Flower

Figure 1:
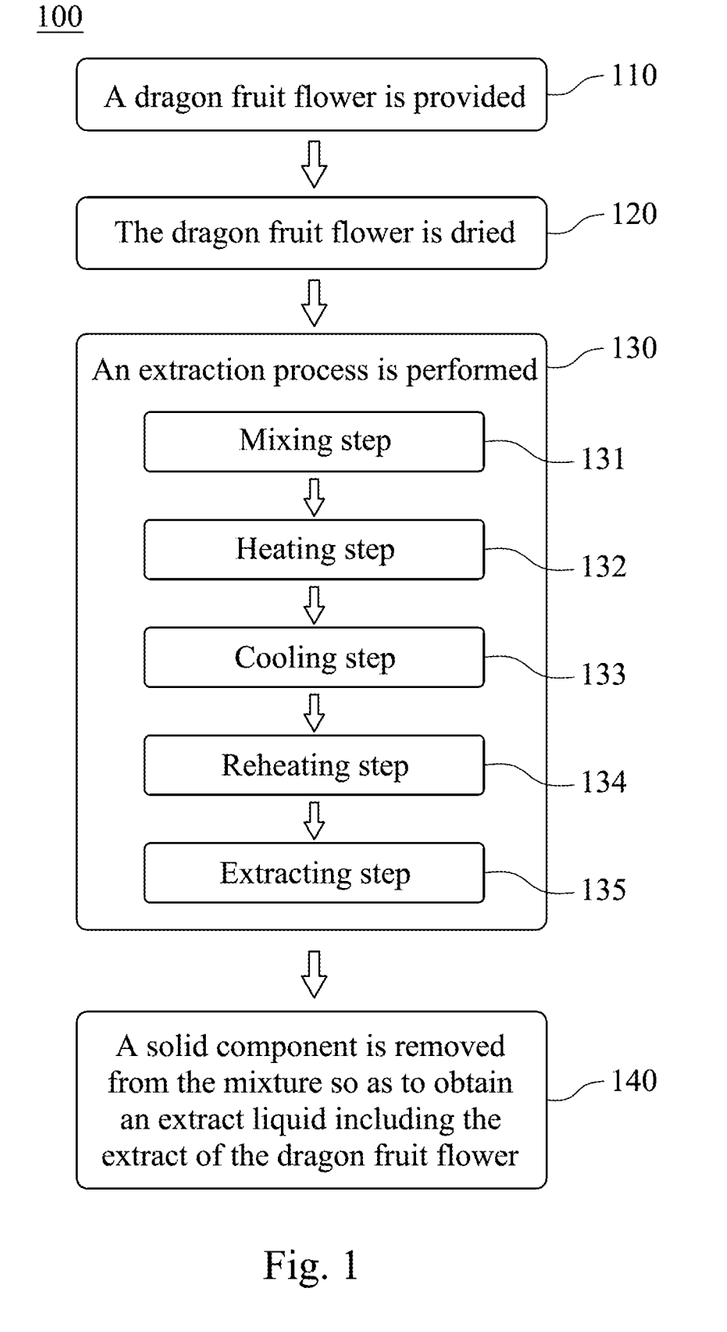
FIG. 1 is a flow chart of a method for preparing an extract of a dragon fruit flower according to one embodiment of the present disclosure.

Please refer to FIG. 1, which is a flow chart of a method 100 for preparing an extract of a dragon fruit flower according to one embodiment of the present disclosure, wherein the method 100 for preparing the extract of the dragon fruit flower includes Step 110, Step 120, Step 130 and Step 140.

In Step 110, a dragon fruit flower is provided, wherein the dragon fruit is a fruit of a perennial plant of genus *Hylocereus* or genus *Selenicereus* of family Cactaceae, and the flowers thereof are rich in polysaccharides and flavonoids with antioxidant activity.

In Step 120, the dragon fruit flower is dried, and then the dragon fruit flower is cut into chips after drying so as to obtain a plurality of dragon fruit flower pieces. The moisture contained in the dragon fruit flower can be removed by drying the dragon fruit flower so as to prevent the purity of the extract of the dragon fruit flower and the concentration of the effective components in the extract of the dragon fruit flower from affecting by the excess moisture.

In Step 130, an extraction process is performed, wherein the extraction process includes a mixing step 131, a heating step 132, a cooling step 133, a reheating step 134 and an extracting step 135. In the mixing step 131, an alcohol solution is mixed with the dragon fruit flower pieces, wherein a weight ratio of the dragon fruit flower pieces to the alcohol solution can range from 1:1 to 1:10 so as to form a mixture of the alcohol solution and the dragon fruit flower pieces; more preferably, the weight ratio of the dragon fruit flower pieces to the alcohol solution can range from 1:2 to 1:6. Furthermore, the alcohol solution can be a glycerol solution with a volume percent concentration ranging from 10% to 50%; more preferably, the volume percent concentration of the glycerol solution can range from 15% to 40%. In the heating step 132, the mixture is heated up to a heating temperature and then is reacted for a heating time, wherein the heating temperature can range from 40° C. to 70° C.; more preferably, the heating temperature can range from 50° C. to 60° C., and the heating time can range from 6 hours to 10 hours; more preferably, the heating time can be 8 hours. In the cooling step 133, the mixture is cooled down to a room temperature and then is rested for a cooling time, wherein the cooling time can range from 20 hours to 28 hours; more preferably, the cooling time can be 24 hours. In the reheating step 134, the mixture is heated up to a reheating temperature and then is reacted for a reheating time, wherein the reheating temperature can range from 40° C. to 70° C.; more preferably, the reheating temperature can range from 50° C. to 60° C., and the reheating time can range from 6 hours to 10 hours; more preferably, the reheating time can be 8 hours. In the extracting step 135, the mixture which has been processed by the reheating step 134 is cooled down to the room temperature and then is stirred and reacted for an extracting time, wherein the extracting time can range from 5 days to 9 days; more preferably, the extracting time can be 7 days.

In Step 140, a solid component is removed from the mixture so as to obtain an extract liquid including the extract of the dragon fruit flower. After processing by Step 110, Step 120 and Step 130, the effective components and the bioactive ingredients of the dragon fruit flower are extracted into the alcohol solution, so that after removing the solid component of the mixture, the remaining liquid component includes the extract of the dragon fruit flower. Furthermore, the solid component can be removed by a centrifugation method, a filtration method, or the combination thereof.

The present disclosure will be further exemplified by the following specific embodiments so as to facilitate utilizing and practicing the present disclosure completely by the people skilled in the art without over-interpreting and over-experimenting. However, the readers should understand that the present disclosure should not be limited to these practical details thereof, that is, in some embodiments, these practical details are used to describe how to implement the materials and methods of the present disclosure and are not necessary.

EXPERIMENTS AND EXAMPLES

I. Preparing an Extract of a Dragon Fruit Flower

In the preparing process of an extract of a dragon fruit flower, the dragon fruit flower is rinsed several times with water and rinsed with distilled water finally, and then remained water is drained from the dragon fruit flower. Next, the water-drained dragon fruit flower is placed in an oven and dried at a temperature below 50° C. for 6 hours. After completely dried, the dragon fruit flower is cut into small chips or is broken by a juice machine so as to obtain a plurality of dragon fruit flower pieces.

After obtaining the dragon fruit flower pieces by the aforementioned method, an extraction process is performed. First, the dragon fruit flower pieces are soaked in an alcohol solution, and a weight ratio of the dragon fruit flower pieces to the alcohol solution ranges from 1:2 to 1:6, wherein the alcohol solution can be an ethanol solution, a butanediol solution or a glycerol solution; more preferably, the alcohol solution is a glycerol solution with a volume percent concentration ranging from 15% to 40%. The dragon fruit flower pieces are well mixed with the alcohol solution so as to form a mixture. Next, the mixture is heated up to 50° C. to 60° C. and then is reacted for 8 hours. After reacting for 8 hours, the mixture is cooled down to a room temperature, and then after cooling for 24 hours, the mixture is further heated up to 50° C. to 60° C. for 8 hours and is cooled again so as to increase the efficiency of extraction. Then, the mixture is soaked and stirred in the alcohol solution at a room temperature for 7 days so as to extract the effective components and bioactive ingredients of the dragon fruit flower.

After finishing the aforementioned extraction steps, the mixture is filtered with a gauze to remove a solid component of the mixture so as to obtain an alcohol extract of the dragon fruit flower including the extract of the dragon fruit flower.

In order to analysis the bioactivities and efficacy of the alcohol extract of the dragon fruit flower, the following experiments are further progressed to assess the effects of the alcohol extract of the dragon fruit flower and the skin complexion improved composition including the alcohol extract of the dragon fruit flower so as to verify the efficacy of the alcohol extract of the dragon fruit flower of the present disclosure.

II. Assessing the Antioxidant Activity of the Extract of the Dragon Fruit Flower Tissues of body must depend on oxidation reactions so as to undergo metabolism thereof and maintain the functions and the vitality thereof. However, there is about 2% to 3% of total oxygen will transform into reactive oxygen species (ROS) and generate many free radicals, wherein the reactive oxygen species are relatively active due to the presence of non-paired electrons, so that the reactive oxygen species can cause aging and death of cells easily and further harm the living organism seriously.

Therefore, the following experiments will assess the antioxidant activity of a glycerol extract of the dragon fruit flower of the present disclosure by performing ferrous ion chelating ability test and DPPH free radical scavenging activity test.

1. Assessing the Ferrous Ion Chelating Ability of the Extract of the Dragon Fruit Flower Ferrous ion ($Fe^{2+}$) is a prooxidant with high reducing activity among a variety of metal ions. In methanol solution, $Fe^{2+}$ can be chelated by ferrozine so as to form red Ferrozine-$Fe^{2+}$ complexes, wherein Ferrozine-$Fe^{2+}$ complexes have a strong absorbance value at wavelength 562 nm. When one ingredient of a solution binds to $Fe^{2+}$, the formation of the Ferrozine-$Fe^{2+}$ complexes will be reduced and then the absorbance value at wavelength 562 nm is lowered correspondingly, so that the ferrous ion chelating ability of a sample can be further evaluated by the degree of reduction of the absorbance value at wavelength 562 nm. Therefore, this experiment will assess the antioxidant activity of the glycerol extract of the dragon fruit flower by the ferrous ion chelating ability thereof, and when the more ferrous ions are chelated, the stronger antioxidant activity of the glycerol extract of the dragon fruit flower.

First, the glycerol extract of the dragon fruit flower is prepared in a form of a methanol solution in the present experiment, and 4.7 mL of the methanol solution including the glycerol extract of the dragon fruit flower is mixed with 0.1 mL of a 2 mM $FeCl_2 \cdot 4H_2O$ solution and then is reacted for 30 seconds. Next, 0.2 mL of 5 mM ferrozine solution is added therein and reacted for 30 minutes in dark at the room temperature, and then the absorbance value of the sample at wavelength 562 nm is detected by a spectrophotometer. Furthermore, in order to further assess the ferrous ion chelating ability of the glycerol extract of the dragon fruit flower, a potent cationic chelating agent EDTA is used in the present experiment as Control group so as to compare with the ferrous ion chelating ability of the glycerol extract of the dragon fruit flower of the present disclosure. The aforementioned experiment is subjected to three repetitions and the values of the ferrous ion chelating rate obtained from the three experiments are plotted in to a diagram so as to facilitate the following analysis, and Formula I which is for calculating the ferrous ions chelating rate is shown below:

$$\text{Ferrous ions chelating rate (\%)} = \left(1 - \frac{\text{Sample 562 nm}}{\text{Control 562 nm}}\right) \times 100\%, \quad \text{(Formula I)}$$

wherein Sample 562 nm is an absorbance value of the sample at wavelength 562 nm, and Control 562 nm is an absorbance value of Control group at wavelength 562 nm.

Figure 2:
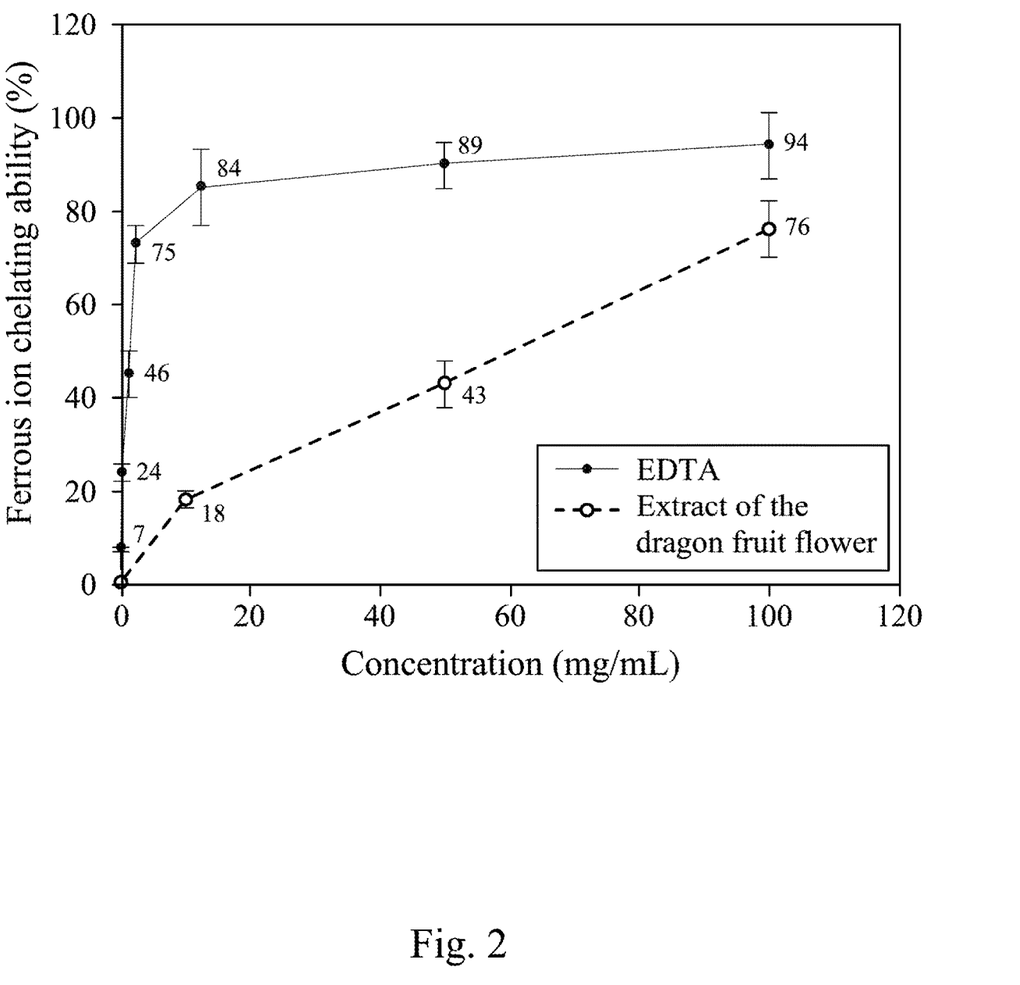
FIG. 2 is a line chart of the ferrous ion chelating rate of a glycerol extract of the dragon fruit flower according to another embodiment of the present disclosure.

Please refer to FIG. 2, which is a line chart of the ferrous ion chelating rate of the glycerol extract of the dragon fruit flower according to another embodiment of the present disclosure. As shown in the results, when a concentration of the methanol solution of the glycerol extract of the dragon fruit flower is 100 mg/mL, compared to the ferrous ion chelating rate of 100 mg/mL EDTA, which is 94%, the ferrous ion chelating rate of the glycerol extract of the dragon fruit flower can reach to 76±6%. It shows that the glycerol extract of the dragon fruit flower of the present disclosure has a good antioxidant ability and has a well potential for fabricating antioxidant drugs.

2. Assessing the DPPH Free Radical Scavenging Activity of the Extract of the Dragon Fruit Flower DPPH (1,1-Diphenyl-2-picrylhydrazyl) is a fairly stable free radical, and an ethanol solution thereof is a blue-violet solution which has a strong absorbance value at wavelength 517 nm. When DPPH free radical is removed by an antioxidant, the absorbance value at wavelength 517 nm will decrease. Therefore, when a greater decreasing level of the absorbance value at wavelength 517 nm is, the antioxidant ability of the sample is better, so that the present experiment will assess the antioxidant activity of the glycerol extract of the dragon fruit flower of the present disclosure by the DPPH free radical scavenging activity thereof.

In the present experiment, 250 μL of freshly prepared ethanol solutions of the glycerol extract of the dragon fruit flower with different concentrations are added into different Eppendorf tubes, respectively, and then 750 μL of 0.1 mM DPPH ethanol solution is added into each of the Eppendorf tubes and then is reacted for 30 minutes in dark at a room temperature after homogeneously mixing. Next, the absorbance value of the aforementioned sample at wavelength 517 nm is detected by a spectrophotometer. Furthermore, an antioxidant BHT (Di-Butyl Hydroxy Toluene) is used in the present experiment as Control group so as to analysis the DPPH free radical scavenging activity of the glycerol extract of the dragon fruit flower of the present disclosure. The aforementioned experiment is subjected to three repetitions and the values of the DPPH free radical scavenging rate obtained from the three experiments are plotted in to a diagram so as to facilitate the following analysis, and Formula II which is for calculating the DPPH free radical scavenging rate is shown below.

$$DPPH \text{ free radical scavenging rate (\%)} = \quad \text{(Formula II)}$$
$$\left(1 - \frac{\text{Sample 517 nm}}{\text{Control 517 nm}}\right) \times 100\%,$$

wherein Sample 517 nm is an absorbance value of the sample at wavelength 517 nm, and Control 517 nm is an absorbance value of Control group at wavelength 517 nm.

Figure 3:
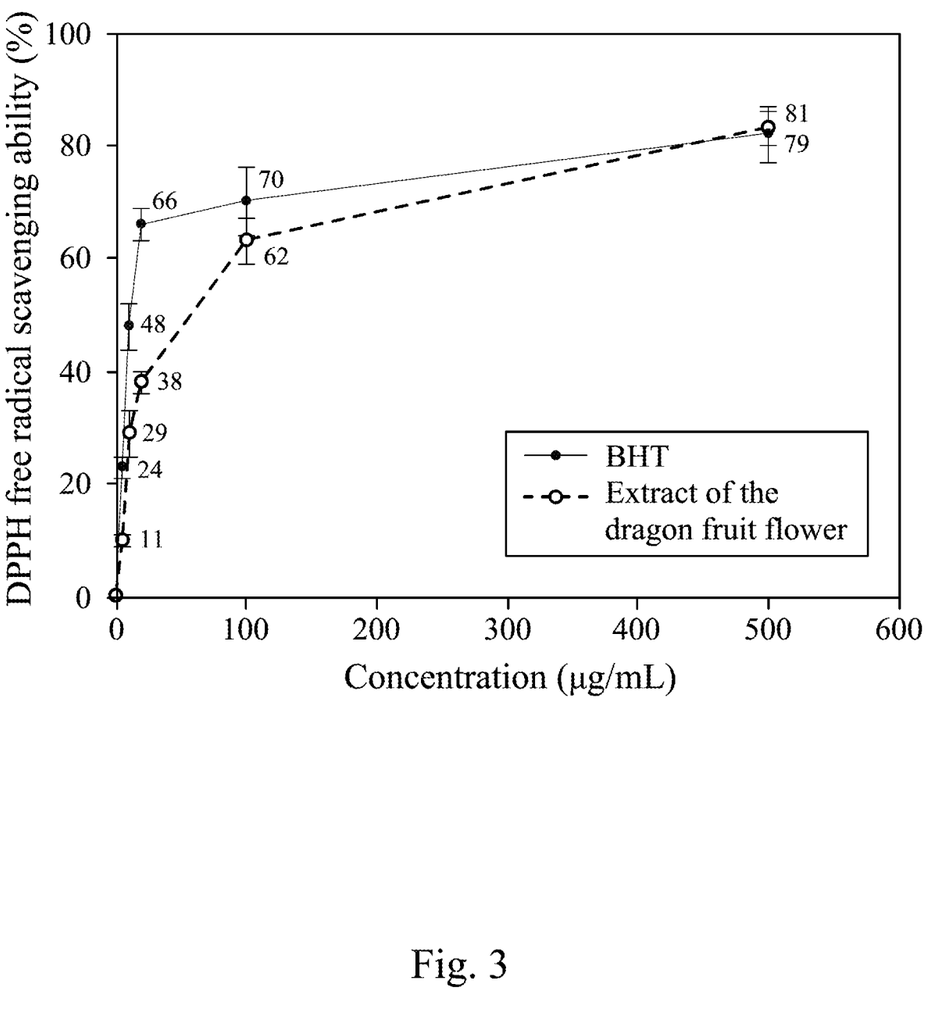
FIG. 3 is a line chart of the DPPH free radical scavenging rate of a glycerol extract of the dragon fruit flower according to another embodiment of the present disclosure.

Please refer to FIG. 3, which is a line chart of the DPPH free radical scavenging rate of the glycerol extract of the dragon fruit flower according to another embodiment of the present disclosure. As shown in the results, when a concentration of the glycerol extract of the dragon fruit flower is 10 μg/mL, the DPPH free radical scavenging rate thereof is 30%, and when a concentration of the glycerol extract of the dragon fruit flower is 100 μg/mL, compared to BHT with the same concentration that the DPPH free radical scavenging rate is 70%, the DPPH free radical scavenging rate of the glycerol extract of the dragon fruit flower can reach more than 60%. Furthermore, when a concentration of the glycerol extract of the dragon fruit flower is 500 μg/mL, the DPPH free radical scavenging rate thereof can further reach to 81%. It shows that the glycerol extract of the dragon fruit flower of the present disclosure has a good DPPH free radical scavenging ability of antioxidant ability and has a well potential for fabricating antioxidant drugs.

It must be noted that, in addition to being administered in an external manner, the glycerol extract of the dragon fruit flower of the present disclosure can also be an oral drug, and the oral drug can be a capsule, a suspension, a powder or a tablet, and the present disclosure is not limited thereto.

III. Assessing the Efficacy of Promoting Wound Healing of the Extract of the Dragon Fruit Flower

1. Assessing the Promoting Ability of the Extract of the Dragon Fruit Flower for Cell Proliferation of the Fibroblast Cells In this experiment, the promoting ability for cell proliferation of the fibroblast cells of the extract of the dragon fruit flower of the present disclosure is evaluated by the cell proliferation rate of the fibroblast cells obtained by MTT assay. The human fibroblast cells CCD-966SK are used in the present experiment, wherein the CCD-966SK fibroblast cell line purchased from Bioresource Conservation and Research Center (BCRC, No. 60153) is a cell line taken from the breast skin of an adult patient with ductal carcinoma so as to verify the promoting ability of the extract of the dragon fruit flower of the present disclosure for cell proliferation of the fibroblast cells.

In the present experiment, the CCD-966SK fibroblast cells are seeded in a 96-well plate in a density of $6 \times 10^3$ cells per well and incubated in the incubator with 5% $CO_2$ at 37° C. for 24 hours. After incubating for 24 hours, the medium is replaced with a new one, and the CCD-966SK fibroblast cells in different wells are treated with the glycerol extract of the dragon fruit flower with different concentrations, respectively. The present experiment is performed with four different concentrations of the glycerol extract of the dragon fruit flower, wherein a glycerol extract of the dragon fruit flower used to treated the CCD-966SK fibroblast cell is 5 mg/ml in Example 1 (Em 1), a glycerol extract of the dragon fruit flower used to treated the CCD-966SK fibroblast cell is 2.5 mg/ml in Example 2 (Em 2), a glycerol extract of the dragon fruit flower used to treated the CCD-966SK fibroblast cell is 1.25 mg/ml in Example 3 (Em 3), and a glycerol extract of the dragon fruit flower used to treated the CCD-966SK fibroblast cell is 0.5 mg/ml in Example 4 (Em 4). Furthermore, in the present experiment, glycerol solutions without the glycerol extract of the dragon fruit flower of the present disclosure are used as comparative examples so as to evaluate the cell proliferation of the CCD-966SK fibroblast cell without the extract of the dragon fruit flower, wherein the CCD-966SK fibroblast cells of Comparative Example 1 (CEm 1) are treated with a 5 mg/ml glycerol solution, the CCD-966SK fibroblast cells of Comparative Example 2 (CEm 2) are treated with a 2.5 mg/ml glycerol solution, the CCD-966SK fibroblast cells of Comparative Example 3 (CEm 3) are treated with a 1.25 mg/m glycerol solution, and the CCD-966SK fibroblast cells of Comparative Example 4 (CEm 4) are treated with a 0.5 mg/ml glycerol solution. After treating for 24 hours and 48 hours, 10 μL of MTT solution is added into each of the wells and then incubated at 37° C. for 4 hours, and absorbance values of the samples at wavelength 570 nm are detected by a spectrophotometer, respectively. Furthermore, the absorbance values at wavelength 570 nm of Example 1 to Example 4 and Comparative Example 1 to Comparative Example 3 are standardized with Comparative Example 4, and then the relative cell proliferation rates of the fibroblast cells of Example 1 to Example 4 are calculated by following Formula III, wherein each of the relative cell proliferation rates of Example 1 to Example 4 is calculated with the relative cell proliferation rate of Comparative Example 1 to Comparative Example 4 which have corresponding concentrations, respectively. Each of Example 1 to Example 4 as well as Comparative Example 1 to Comparative Example 4 is subjected to two repetitions.

$$\text{Relative cell proliferation rate (\%)} = \frac{\text{Absorbance value of Example } Y_{(X \text{ hours})} - \text{Absorbance value of Comparative example } Y_{(X \text{ hours})}}{\text{Absorbance value of Comparative example } Y_{(X \text{ hours})}} \times 100, \quad \text{(Formula III)}$$

wherein, $X = 12$ or $24$, and $Y = 1, 2, 3$ or $4$.

Figure 4A:
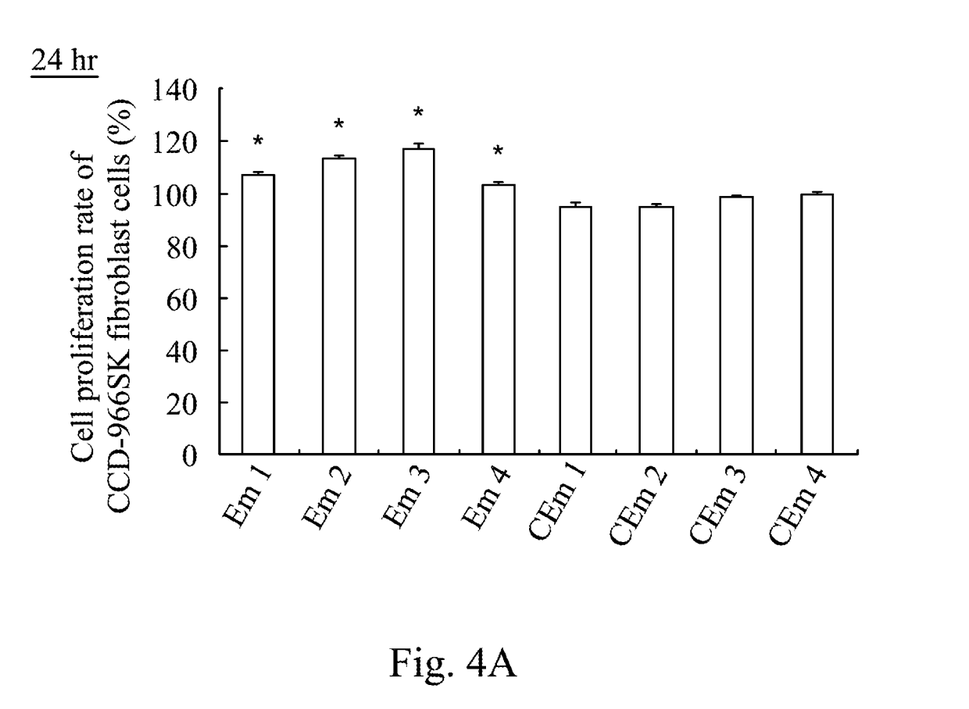
FIG. 4A is a histogram of the cell proliferation rate of CCD-966SK fibroblast cells after treating with a glycerol extract of the dragon fruit flower for 24 hours according to further another embodiment of the present disclosure.
Figure 4B:
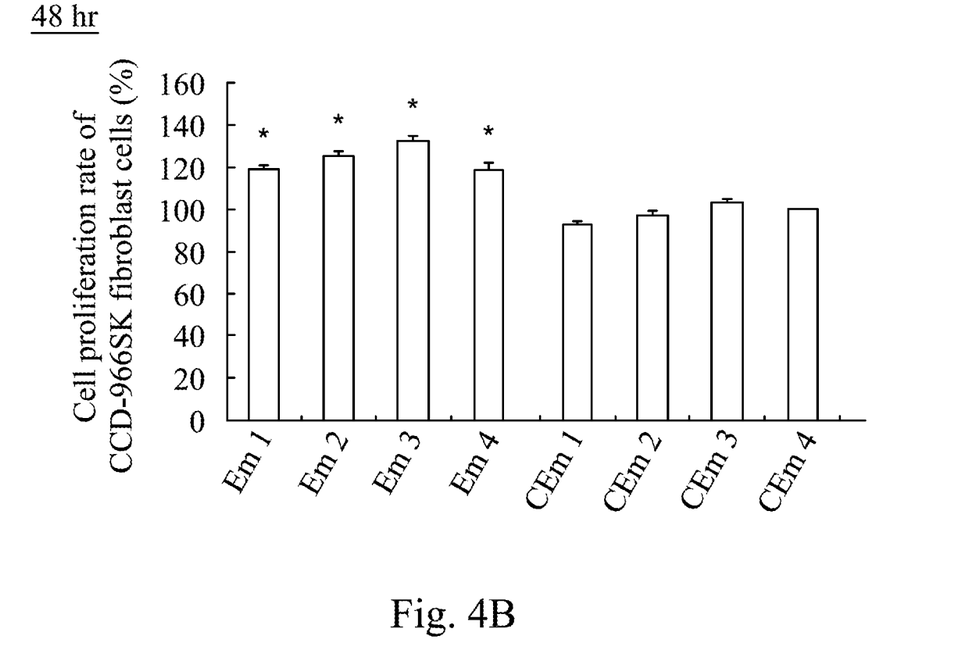
FIG. 4B is a histogram of the cell proliferation rate of the CCD-966SK fibroblast cells after treating with the glycerol extract of the dragon fruit flower for 48 hours according to further another embodiment of the present disclosure.

Furthermore, in the present experiment, a statistical analysis of the relative cell proliferation rates of Example 1 to Example 4 and Comparative Example 1 to Comparative Example 3 to the relative cell proliferation rate of the fibroblast cells of Comparative Example 4 are progressed, respectively. The symbol "*" marked on the histogram presents a statistical significance ($p<0.05$) between the relative cell proliferation rates of aforementioned examples with Comparative Example 4, so as to compare and explain that the glycerol extract of the dragon fruit flower of the present disclosure has a better ability for promoting cell proliferation of fibroblast cells.

Please refer to FIG. 4A and FIG. 4B, FIG. 4A is a histogram of the cell proliferation rate of the CCD-966SK fibroblast cells after treating with the glycerol extract of the dragon fruit flower for 24 hours according to further another embodiment of the present disclosure, and FIG. 4B is a histogram of the cell proliferation rate of the CCD-966SK fibroblast cells after treating with the glycerol extract of the dragon fruit flower for 48 hours according to further another embodiment of the present disclosure. In detail, in FIG. 4A and FIG. 4B, each of the cell proliferation rates obtained by the Formula III is added 100% for serving as a benchmark of fibroblast cell proliferation so as to verify additional proliferative effects of the glycerol extract of the dragon fruit flower of the present disclosure on the CCD-966SK fibroblast cells under normal growth conditions. As shown in FIG. 4A and FIG. 4B, after treating with the glycerol solutions of Comparative Example 1 to Comparative Example 3 which are not treated with the glycerol extract of the dragon fruit flower of the present disclosure for 24 hours and 48 hours, there is no significant difference between the cell proliferation rates of the CCD-966SK fibroblast cells thereof and Comparative Example 4, so that the cell proliferation rates of the CCD-966SK fibroblast cells are not affected by the glycerol solutions which are without the extract of the dragon fruit flower of the present disclosure. Furthermore, after treating for 24 hours and 48 hours with the glycerol extracts of the dragon fruit flower of the present disclosure of Example 1 to Example 4 with different concentration, respectively, the cell proliferation rates of Example 1 to Example 4 are better than the cell proliferation rates of Comparative Example 1 to Comparative Example 4 under a condition of the same concentration. In particular, the cell proliferation rate of the CCD-966SK fibroblast cells of Example 3 is best, and the cell proliferation rates thereof at 24 hours and 48 hours compared to Comparative Example 4 increase 14% and 32%, respectively.

As shown in the aforementioned results, the glycerol extract of the dragon fruit flower of the present disclosure has an excellent effect for promoting the cell proliferation of fibroblast cells and has an excellent potential for promoting wound healing.

2. Assessing the Promoting Ability of the Extract of the Dragon Fruit Flower for Cell Migration of Fibroblast Cells Many studies have proved that fibroblast cells can proliferate and migrate to the wound in a short time and thus promote the repair and healing of the wound, so that in this experiment, an in vitro wound healing test of the CCD-966SK fibroblast cells is used to evaluate the promoting effect of the crawling ability of the glycerol extract of the dragon fruit flower of the present disclosure, and the migrated distance in the simulated wound of the cells is used for assessing the migration ability of the CCD-966SK fibroblast cells.

In the present experiment, the CCD-966SK fibroblast cells are seeded in the two chambers of a cell spacer in a density of $5 \times 10^4$ cells per chamber and then incubated in the incubator with 5% $CO_2$ at 37° C. for 24 hours. After incubating for 24 hours, the cell spacer is removed so that a gap of 500 μm in width is formed between the CCD-966SK fibroblast cells seeded in the two chambers so as to simulate a wound on the living organism. Then, the CCD-966SK fibroblast cells are treated with the medium including the glycerol extracts of the dragon fruit flower of the aforementioned Example 1 to Example 4, respectively, and a cell distribution condition at this time is served as a wound width at 0 hour (that is, the time point of wound formation) and is recorded by a light microscope. After treating with the glycerol extracts of the dragon fruit flower for 12 hours and 24 hours, wound widths of Example 1 to Example 4 which have different concentrations of the glycerol extract of the dragon fruit flower of the present disclosure are further recorded and measured, respectively, and the wound repair rates thereof are calculated by the following Formula IV:

$$\text{Wound repair rate } (\%) = \frac{\text{Wound width}_{(0\ hour)} - \text{Wound width}_{(X\ hour)}}{\text{Wound width}_{(0\ hour)}} \times 100, \quad \text{(Formula IV)}$$

wherein, X=12 or 24. Furthermore, the aforementioned Comparative Example 1 to Comparative Example 4, as well as a Control group which is without any treatment of the glycerol extract of the dragon fruit flower or a glycerol solution are used in the present experiment so as to assess the promoting effect of the crawling ability of the glycerol extract of the dragon fruit flower of the present disclosure on fibroblast cells.

Figure 5:
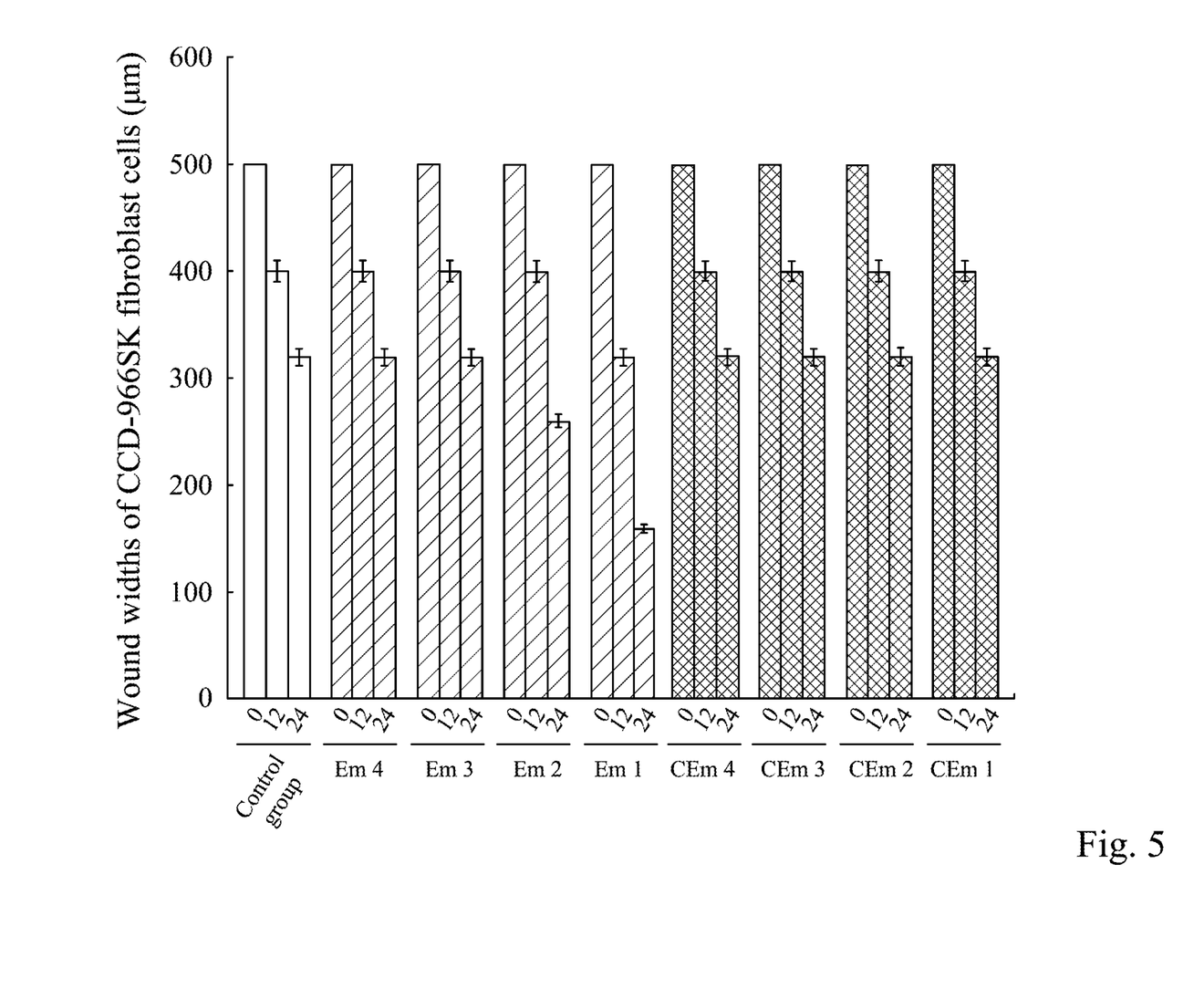
FIG. 5 is a histogram of the wound widths of the in vitro wound healing test of the CCD-966SK fibroblast cells after treating with the glycerol extract of the dragon fruit flower for 0 hour, 12 hours and 24 hours according to further another embodiment of the present disclosure.

Please refer to FIG. 5, which is a histogram of the wound widths of the in vitro wound healing test of the CCD-966SK fibroblast cells after treating with the glycerol extract of the dragon fruit flower for 0 hour, 12 hours and 24 hours according to further another embodiment of the present disclosure. As shown in FIG. 5 after growing for 12 hours and 24 hours, the wound widths of Control group are 400 m and 320 μm, respectively, that is, a natural wound repair rate of the CCD-966SK fibroblast cells after 12 hours of the wound formation is about 20%, and a natural wound repair rate of the CCD-966SK fibroblast cells after 24 hours of the wound formation is about 36%. In the results of the wound repair rates of the CCD-966SK fibroblast cells of Comparative Example 1 to Comparative Example 4, after 12 hours of the wound formation, the wound repair rates of Comparative Example 1 to Comparative Example 4 are about 20%, and after 24 hours of the wound formation, the wound repair rates of Comparative Example 1 to Comparative Example 4 are about 36%. Furthermore, in the results of the wound repair rates of the CCD-966SK fibroblast cells of Example 1 to Example 4 which are treated with the glycerol extract of the dragon fruit flower of the present disclosure, after 24 hours of the wound formation, the wound repair rates are 36% of Example 1, 36% of Example 2, 48% of Example 3 and 68% of Example 4, which have better performances compared to all of the wound repair rates of Comparative Example 1 to Comparative Example 4. It shows that the glycerol extract of the dragon fruit flower of the present disclosure has an excellent ability for promoting cell migration of fibroblast cells and has a well potential for fabricating drugs for enhancing wound healing.

It must be noted that, in addition to being administered in an external manner, the drugs for enhancing wound healing including the glycerol extract of the dragon fruit flower of the present disclosure can also be an oral drug, and the oral drug can be a capsule, a suspension, a powder or a tablet, and the present disclosure is not limited thereto.

IV. Assessing the Efficacy of the Skin Complexion Improved Composition Including the Extract of the Dragon Fruit Flower The present disclosure provides a skin complexion improved composition including an effective amount of an extract of a dragon fruit flower, wherein the extract of the dragon fruit flower is prepared by the aforementioned method for preparing the extract of the dragon fruit flower. In the present embodiment, a lotion of the extract of the dragon fruit flower which is made of the ingredients of Table 1 is provided.

TABLE 1

| Percentage (%) | Ingredient |
| --- | --- |
| A phase | |
| 2.0 | Olive emulsifying wax |
| 2.0 | Stearic acid |
| 2.6 | Jojoba oil |
| 5.3 | Finsolv TN |
| 3.3 | Lipovol MOS 70 |
| 0.3 | Dimethicon |

TABLE 1-continued

| Percentage (%) | Ingredient |
|---|---|
| 0.1 | Tocapheryl Acetate |
| 0.2 | Uniphon P-23 (preservative) |
| | B phase |
| 2.0 | Propylene Glycol |
| 2.0 | Butanediol |
| 2.0 | 1% Sodium Hyaluron |
| 5.0 | extract of the dragon fruit flower |
| 0.6 | Germaben II (preservative) |
| 0.1 | Disadium EDTA |
| 0.1 | Triethanolamine (TEA) |
| 71.2 | Distilled water |

In the preparing method of the lotion of the extract of the dragon fruit flower, all of the ingredients of B phase are added into a container and mixed homogeneously, and then the ingredients of B phase are heated up to 70° C. to 75° C. with stirring until all of the ingredients thereof are dissolved. In the same time, all of the ingredients of A phase are added into another container and mixed homogeneously, and then the ingredients of A phase are heated up to 70° C. to 75° C. with stirring until all of the ingredients thereof are dissolved. Next, a mixture of Phase A maintaining at 70° C. to 75° C. is mixed with a mixture of Phase B maintaining at 70° C. to 75° C. and stirred quickly for 5 minutes and then processed by a homogenizer for 3 minutes. After processing for 3 minutes, a mixture of the mixture of Phase A and the mixture of Phase B is stirred with a stirrer until a temperature of the mixture thereof is cooled down to the room temperature so as to obtain the lotion of the extract of the dragon fruit flower of the present embodiment.

In order to assess the effects of the lotion of the extract of the dragon fruit flower for improving the skin complexion, in the present experiment, each of a lotion of the ethanol extract of the dragon fruit flower, a lotion of the butanediol extract of the dragon fruit flower, a lotion of the glycerol extract of the dragon fruit flower and a glycerol lotion (which is not treated with the extract of the dragon fruit flower) is processed by the long-lasting moisturizing ability test, the short-acting moisturizing ability test, the reducing rate of the skin melanin index test and the skin brightness enhancing rate test.

1. Assessing of the Long-Lasting Moisturizing Ability of the Lotion of the Extract of the Dragon Fruit Flower The skin keratin moisture content can be evaluated by the capacitance of the skin, so that a non-invasive skin capacitance tester Corneometer® CM 825 (Courage-Khazaka Electronic, Cologne, Germany) is used to detect the moisture content of superficial epithelium to 0.1 mm of subcutaneous tissue in this experiment. There are five experimental groups in the present experiment, and those are the lotion of the ethanol extract of the dragon fruit flower, the lotion of the butanediol extract of the dragon fruit flower, the lotion of the glycerol extract of the dragon fruit flower, the glycerol lotion, and a placebo. Skin conditions of the subjects of each of the experimental groups are measured in a cosmetics effectiveness evaluation room before using the lotions of the extracts of the dragon fruit flower, wherein an environmental temperature of the cosmetics effectiveness evaluation room is 22±1° C. and a relative humidity thereof is 60±5%. After 30 minutes of the subjects have cleaned the face, the skin keratin moisture content of the right faces of the subjects before using the lotions of the extracts of the dragon fruit flower are detected by Corneometer® CM 825, and then the subjects are asked to use the lotions of the extracts of the dragon fruit flower after cleaning their face every morning and evening for four weeks and then return to the cosmetics effectiveness evaluation room for post-use testing after four weeks, wherein the test site is also the right face. The aforementioned experiment is subjected to three repetitions and the values of the moisture content improving rates obtained from the three experiments are plotted in to a diagram so as to progress the following analysis, and Formula V which is for calculating the moisture content improving rate of the skin keratin is shown below:

$$\text{Moisture content improving rate of the skin keratin } (\%) = \frac{\text{Post-using keratin moisture content} - \text{Pre-using keratin moisture content}}{\text{Pre-using keratin moisture content}} \times 100. \quad \text{(Formula V)}$$

Figure 6A:
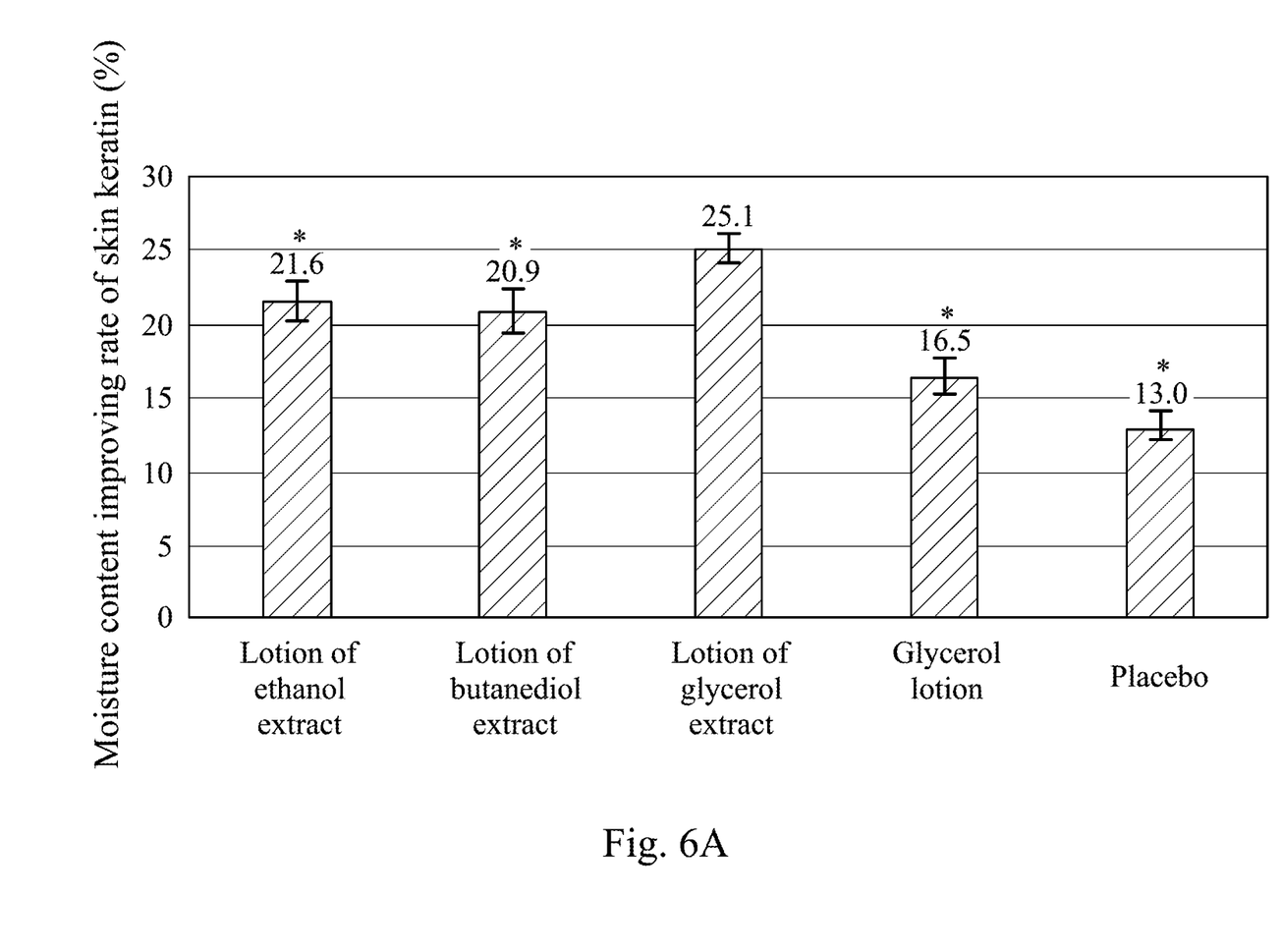
FIG. 6A is a histogram of the moisture content improving rate of the skin keratin of subjects after using lotions of the extracts of the dragon fruit flower for four weeks according to still another embodiment of the present disclosure.
Figure 6B:
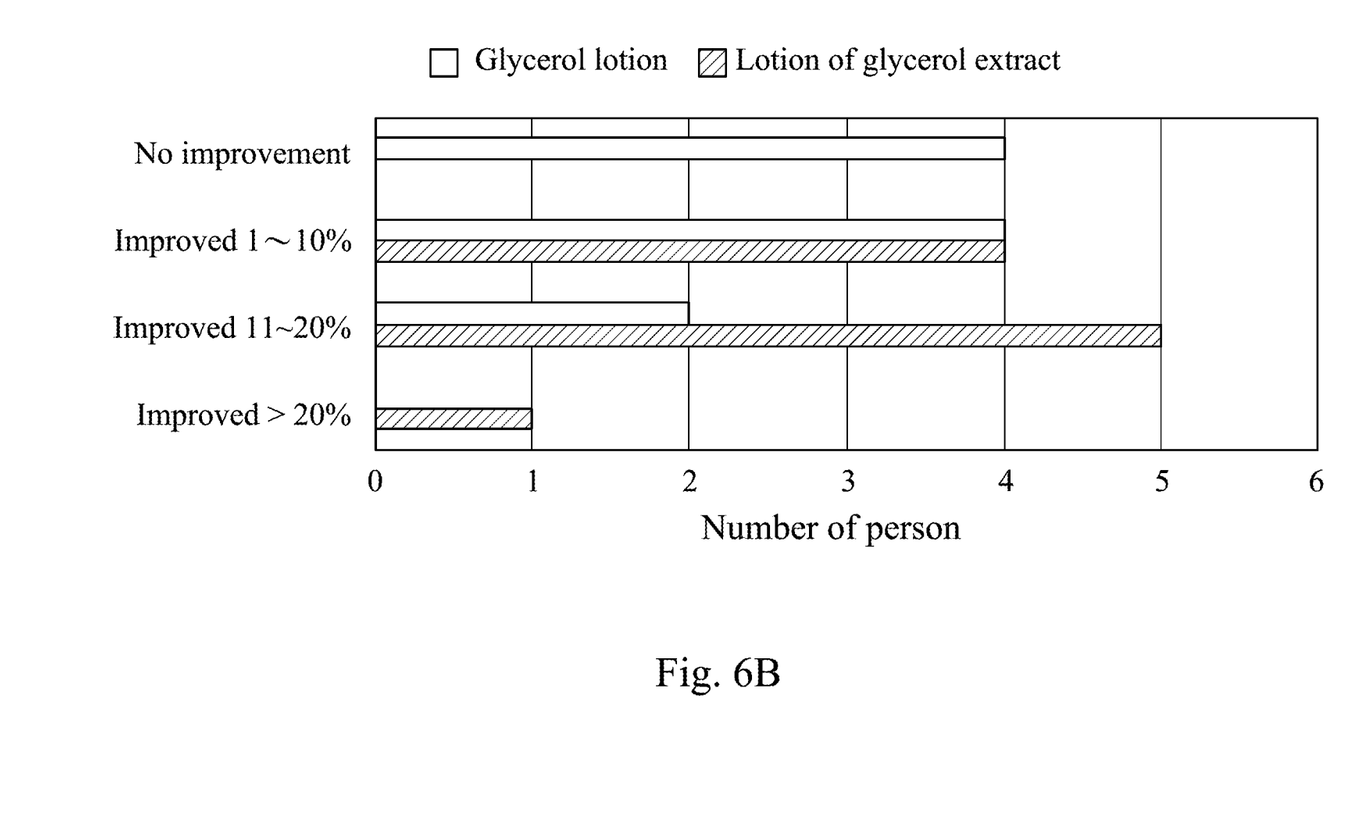
FIG. 6B is a histogram of the number of people who have improved the skin keratin moisture content after using the lotions of the extracts of the dragon fruit flower for four weeks according to still another embodiment of the present disclosure.

Please refer to FIG. 6A and FIG. 6B, FIG. 6A is a histogram of the moisture content improving rate of the skin keratin of subjects after using lotions of the extracts of the dragon fruit flower for four weeks according to still another embodiment of the present disclosure, and FIG. 6B is a histogram of the number of people who have improved the skin keratin moisture content after using the lotions of the extracts of the dragon fruit flower for four weeks according to still another embodiment of the present disclosure. As shown in the results, after using the lotions of the extracts of the dragon fruit flower of the present disclosure for four weeks, the skin keratin moisture content of the lotion of the ethanol extract of the dragon fruit flower increases 21.6%, the skin keratin moisture content of the lotion of the butanediol extract of the dragon fruit flower increases 20.9%, the skin keratin moisture content of the lotion of the glycerol extract of the dragon fruit flower increases 25.1%, the skin keratin moisture content of the glycerol lotion increases 16.5%, and the skin keratin moisture content of the placebo increases 13.0%. The moisture content improving rate of the skin keratin of the lotion of the glycerol extract of the dragon fruit flower is best.

The moisture content improving rates of the skin keratin of the aforementioned experimental groups are further analyzed by T-test. As shown in FIG. 6A, when the lotion of the glycerol extract of the dragon fruit flower is served as a comparative group, the symbol "*" is marked on the histogram presents a statistical significance (p<0.05) between the moisture content improving rates of the skin keratin of the comparative group and other experimental groups. As shown in the results of T-test, the moisture content improving rate of the skin keratin of the lotion of the glycerol extract of the dragon fruit flower has a significantly increase compared to the moisture content improving rates of the skin keratin of the lotion of the ethanol extract of the dragon fruit flower, the lotion of the butanediol extract of the dragon fruit flower, the glycerol lotion and the placebo, respectively. It shows that the ability of the lotions of the glycerol extract of the dragon fruit flower for Improving the skin keratin moisture content is excellent. Detail statistical analysis results of the moisture content improving rate of the skin keratin between the experimental groups are shown in Table 2.

TABLE 2

| Sample | Lotion of butanediol extract | Lotion of glycerol extract | Glycerol lotion | Placebo |
|---|---|---|---|---|
| Lotion of ethanol extract | 0.577 | 0.022* | 0.009* | 0.001* |
| Lotion of butanediol extract | — | 0.014* | 0.016* | 0.001* |
| Lotion of glycerol extract | — | — | 0.001* | 0.001* |
| Glycerol lotion | — | — | — | 0.017* |

*a statistical significance between groups (P < 0.05).

As shown in the statistical results of the number of subjects that the skin complexion has improved, a person number of improving the skin keratin moisture content and an improving level thereof more than 11% after using the lotion of the glycerol extract of the dragon fruit flower is better than the glycerol lotion. It shows that the lotion of the glycerol extract of the dragon fruit flower has an excellent long-lasting moisturizing ability.

2. Assessing of the Short-Acting Moisturizing Ability of the Lotion of the Extract of the Dragon Fruit Flower Hyaluronic acid, which is also called uronic acid or hyaluronan, has high biocompatibility and moisturizing ability so that it is used in the field of aesthetic medicine for relieving dry skin commonly. Thus, in this experiment, lotions including different ratios of hyaluronic acid, the glycerol extract of the dragon fruit flower, as well as hyaluronic acid and the glycerol extract of the dragon fruit flower are used in the short-acting moisturizing ability test, respectively. The non-invasive skin capacitance tester Corneometer® CM 825 is used to detect the moisture content of superficial epithelium to 0.1 mm of subcutaneous tissue in the present experiment.

There are nine experimental groups in the present experiment, wherein Group 1 is a lotion including 5% glycerol extract of the dragon fruit flower and 1% hyaluronic acid, Group 2 is a lotion including 3% glycerol extract of the dragon fruit flower and 1% hyaluronic acid, Group 3 is a lotion including 1% glycerol extract of the dragon fruit flower and 1% hyaluronic acid, Group 4 is a lotion including 5% hyaluronic acid, Group 5 is a lotion including 3% hyaluronic acid, Group 6 is a lotion including 1% hyaluronic acid, Group 7 is a lotion including 5% glycerol extract of the dragon fruit flower, Group 8 is a lotion including 3% glycerol extract of the dragon fruit flower, and Group 9 is a lotion including 1% glycerol extract of the dragon fruit flower. Skin conditions of the subjects of each of the experimental groups are measured in the aforementioned cosmetics effectiveness evaluation room before using the aforementioned lotions. After 30 minutes of the subjects have cleaned the face, the skin keratin moisture content of the right faces of the subjects before using the aforementioned lotions are detected by Corneometer® CM 825, and then the skin keratin moisture content of the right faces of the subjects will detected again after using the aforementioned lotions for 1.5 hours. The aforementioned experiment is subjected to three repetitions and the values of the moisture content improving rate obtained from the three experiments are plotted in to a diagram so as to progress the following analysis, and Formula VI which is for calculating the moisture content improving rate of the skin keratin is shown below:

$$\text{Moisture content improving rate of the skin keratin } (\%) = \frac{\text{Post-using keratin moisture content} - \text{Pre-using keratin moisture content}}{\text{Pre-using keratin moisture content}} \times 100. \quad \text{(Formula VI)}$$

Figure 6C:
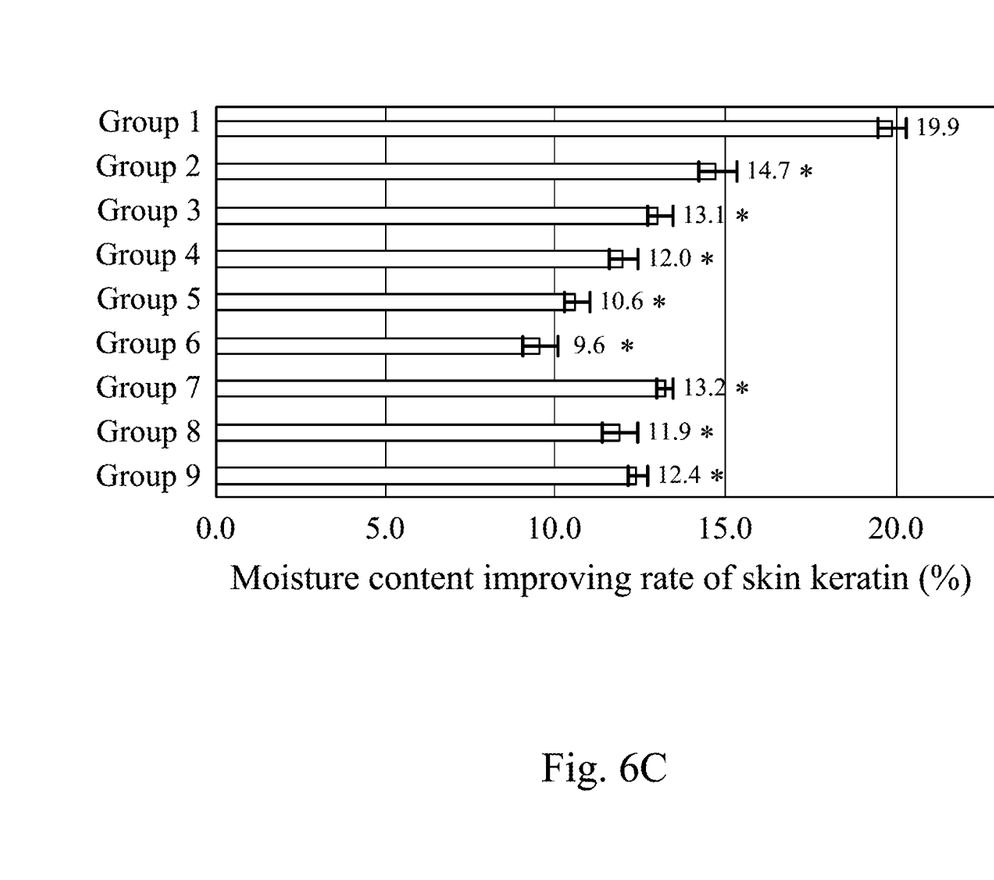
FIG. 6C is a histogram of the moisture content improving rate of the skin keratin of subjects after using the lotions of the extracts of the dragon fruit flower for 1.5 hours according to still another embodiment of the present disclosure.

Please refer to FIG. 6C, which is a histogram of the moisture content improving rate of the skin keratin of subjects after using the lotion of the extract of the dragon fruit flower for 1.5 hours according to still another embodiment of the present disclosure. As shown in the results, among the short-acting test of the lotions including different concentrations of the glycerol extract of the dragon fruit flower and the hyaluronic acid, the moisture content improving rate of the skin keratin of Group 1 is 19.9%, the moisture content improving rate of the skin keratin of Group 2 is 14.7%, the moisture content improving rate of the skin keratin of Group 3 is 13.1%, the moisture content improving rate of the skin keratin of Group 4 is 12.0%, the moisture content improving rate of the skin keratin of Group 5 is 10.6%, the moisture content improving rate of the skin keratin of Group 6 is 9.6%, the moisture content improving rate of the skin keratin of Group 7 is 13.2%, the moisture content improving rate of the skin keratin of Group 8 is 11.9%, and the moisture content improving rate of the skin keratin of Group 9 is 12.4%. It shows that the short-acting moisturizing ability of the lotion including the extract of the dragon fruit flower is excellent, and the moisture content improving rate of the skin keratin thereof is equal to the moisture content improving rate of the skin keratin of the lotion including hyaluronic acid.

The moisture content improving rates of the skin keratin of the aforementioned experimental groups are further analyzed by T-test. As shown in FIG. 6C, when the lotion of Group 1 which includes 5% glycerol extract of the dragon fruit flower and 1% hyaluronic acid is served as a comparative group, the symbol "*" is marked on the histogram presents a statistical significance (p<0.05) between the moisture content improving rates of the skin keratin of the comparative group and other experimental groups. As shown in the results of T-test, the moisture content improving rate of the skin keratin of Group 1 has a significantly increase compared to the moisture content improving rates of the skin keratin of other experimental groups. It shows that the ability for improving the skin keratin moisture content of a lotion including 5% glycerol extract of the dragon fruit flower and 1% hyaluronic acid is excellent. Detail statistical analysis results of the moisture content improving rate of the skin keratin between the experimental groups are shown in Table 3.

TABLE 3

| Sample | Group 2 | Group 3 | Group 4 | Group 5 | Group 6 | Group 7 | Group 8 | Group 9 |
|---|---|---|---|---|---|---|---|---|
| Group 1 | 0.001* | 0.001* | 0.001* | 0.001* | 0.001* | 0.001* | 0.001* | 0.001* |
| Group 2 | — | 0.014* | 0.003* | 0.001* | 0.001* | 0.001* | 0.0038 | 0.001* |
| Group 3 | — | — | 0.028* | 0.001* | 0.001* | 0.718 | 0.028* | 0.053 |

TABLE 3-continued

| Sample | Group 2 | Group 3 | Group 4 | Group 5 | Group 6 | Group 7 | Group 8 | Group 9 |
|---|---|---|---|---|---|---|---|---|
| Group 4 | — | — | — | 0.013* | 0.004* | 0.015* | 0.807 | 0.246 |
| Group 5 | — | — | — | — | 0.054 | 0.001* | 0.022* | 0.002* |
| Group 6 | — | — | — | — | — | 0.001* | 0.005* | 0.001* |
| Group 7 | — | — | — | — | — | — | 0.016* | 0.021* |
| Group 8 | — | — | — | — | — | — | — | 0.201 |

*a statistical significance between groups ($P < 0.05$).

3. Assessing of the Ability for Reducing the Skin Melanin Index of the Lotion of the Extract of the Dragon Fruit Flower In this experiment, the skin melanin index (E) is measured by DSM II Skin ColorMeter (Cortex Technology, Hadsun, Denmark). There are four experimental groups in the present experiment, and those are a lotion of the ethanol extract of the dragon fruit flower, a lotion of the butanediol extract of the dragon fruit flower, a lotion of the glycerol extract of the dragon fruit flower and a placebo. Skin conditions of the subjects of each of the experimental groups are measured in the cosmetics effectiveness evaluation room before using the lotions of the extracts of the dragon fruit flower. After 30 minutes of the subjects have cleaned the face, the skin melanin index of each of the right faces of the subjects before using the aforementioned lotions are detected by DSM II Skin ColorMeter, and then the subjects are asked to use the lotions of the extracts of the dragon fruit flower after cleaning their face every morning and evening for four weeks and then return to the cosmetics effectiveness evaluation room for post-use testing after four weeks, wherein the test site is also the right face. The aforementioned experiment is subjected to three repetitions and the values of the reducing rate of the skin melanin index obtained from the three experiments are plotted in to a diagram so as to progress the following analysis, and Formula VII which is for calculating the reducing rate of the skin melanin index is shown below:

$$\text{Reducing rate of skin melanin index (\%)} = \frac{\text{Pre-using skin melanin index} - \text{Post-using skin melanin index}}{\text{Pre-using skin melanin index}} \times 100\%. \quad \text{(Formula VII)}$$

Figure 7:
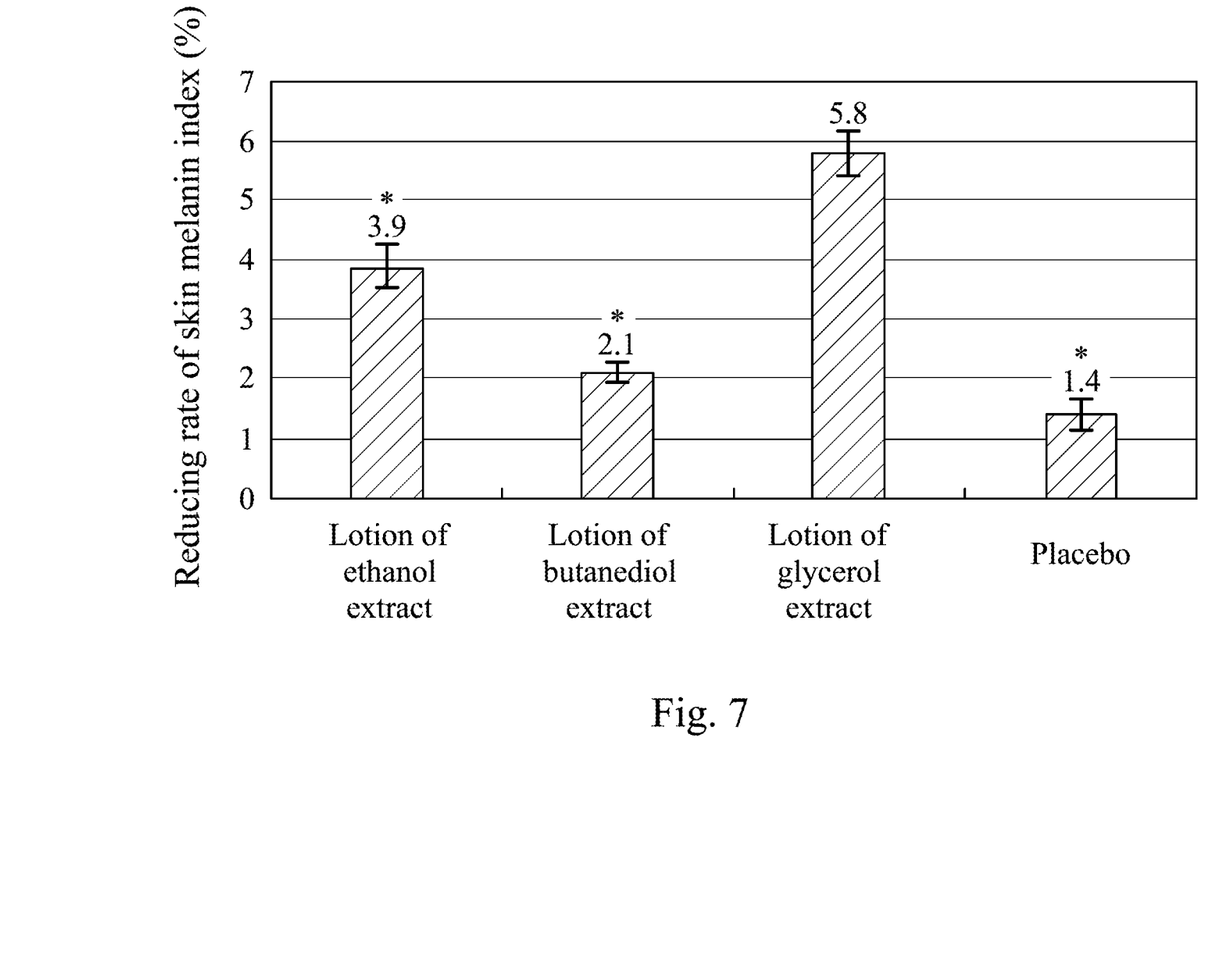
FIG. 7 is a histogram of the reducing rate of the skin melanin index of subjects after using the lotions of the extracts of the dragon fruit flower for four weeks according to yet another embodiment of the present disclosure.

Please refer to FIG. 7, which is a histogram of the reducing rate of the skin melanin index of subjects after using the lotions of the extracts of the dragon fruit flower for four weeks according to yet another embodiment of the present disclosure. As shown in the results, the reducing rate of the skin melanin index of using the lotion of the glycerol extract of the dragon fruit flower for four weeks is 5.8%, which is significantly decreased compared to 3.9% of the lotion of the ethanol extract of the dragon fruit flower, 2.1% of the lotion of the butanediol extract of the dragon fruit flower, and 1.4% of the placebo.

The reducing rates of the skin melanin index of the aforementioned experimental groups are also further analyzed by T-test. As shown in FIG. 7, when the lotion of the glycerol extract of the dragon fruit flower is served as a comparative group, the symbol "*" is marked on the histogram presents a statistical significance (p<0.05) between the reducing rates of the skin melanin index of the comparative group and other experimental groups. As shown in the results of T-test, the reducing rate of the skin melanin index of the lotion of the glycerol extract of the dragon fruit flower for using four weeks has a significantly decrease compared to the reducing rates of the skin melanin index of other experimental groups. It shows that the ability for reducing the skin melanin index of the lotion of the glycerol extract of the dragon fruit flower is excellent. Detail statistical analysis results of the reducing rates of the skin melanin Index between the experimental groups are shown in Table 4.

TABLE 4

| Sample | Lotion of butanediol extract | Lotion of glycerol extract | Placebo |
|---|---|---|---|
| Lotion of ethanol extract | 0.001* | 0.003* | 0.001* |
| Lotion of butanediol extract | — | 0.001* | 0.019* |
| Lotion of glycerol extract | — | — | 0.001* |

*a statistical significance between groups ($P < 0.05$).

4. Assessing the Ability for Enhancing the Skin Brightness of the Lotion of the Extract of the Dragon Fruit Flower In this experiment, the skin brightness index (L*) s measured by DSM II Skin ColorMeter. There are four experimental groups in the present experiment, and those are a lotion of the ethanol extract of the dragon fruit flower, a lotion of the butanediol extract of the dragon fruit flower, a lotion of the glycerol extract of the dragon fruit flower and a placebo. Skin conditions of the subjects of each of the experimental groups are measured in the cosmetics effectiveness evaluation room before using the lotions of the extracts of the dragon fruit flower. After 30 minutes of the subjects have cleaned the face, the skin brightness index of each of the right faces of the subjects before using the aforementioned lotions are detected by DSM II Skin ColorMeter, and then the subjects are asked to use the lotions of the extract of the dragon fruit flower after cleaning their face every morning and evening for four weeks and then return to the cosmetics effectiveness evaluation room for post-use testing after four weeks, wherein the test site is also the right face. The aforementioned experiment is subjected to three repetitions and the values of the increasing rate of the skin brightness index obtained from the three experiments are plotted in to a diagram so as to progress the following analysis, and Formula VIII which is for calculating the increasing rate of the skin brightness index is shown below:

$$\text{Increasing rate of skin brightness index (\%)} = \frac{\text{Pre-using skin brightness index} - \text{Post-using skin brightness index}}{\text{Pre-using skin brightness index}} \times 100\%. \quad \text{(Formula VIII)}$$

Figure 8:
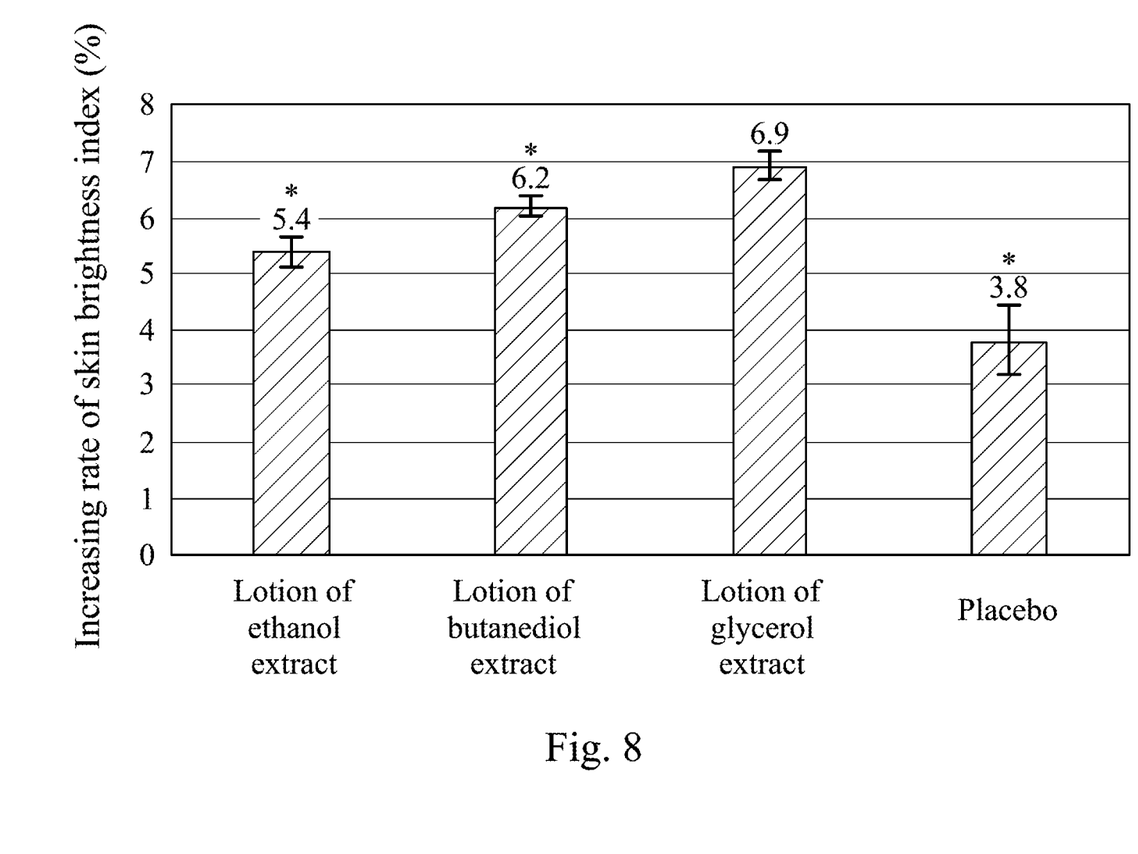
FIG. 8 is a histogram of the skin brightness enhancing rate of the subjects after using the lotions of the extracts of the dragon fruit flower for four weeks according to still further another embodiment of the present disclosure.

Please refer to FIG. 8, which is a histogram of the skin brightness enhancing rate of the subjects after using the lotions of the extracts of the dragon fruit flower for four weeks according to still further another embodiment of the present disclosure. As shown in the results, the increasing rate of the skin brightness index of using the lotion of the glycerol extract of the dragon fruit flower for four weeks is 6.9%, which is significantly increased compared to 5.4% of the lotion of the ethanol extract of the dragon fruit flower, 6.2% of the lotion of the butanediol extract of the dragon fruit flower, and 3.8% of the placebo.

The increasing rates of skin brightness index of the aforementioned experimental groups are also further analyzed by T-test. As shown in FIG. 8, when the lotion of the glycerol extract of the dragon fruit flower is served as a comparative group, the symbol "*" is marked on the histogram presents a statistical significance (p<0.05) between the increasing rates of skin brightness index of the comparative group and other experimental groups. As shown in the results of T-test, the increasing rate of skin brightness index of the lotion of the glycerol extract of the dragon fruit flower for using four weeks has a significantly increase compared to the increasing rate of skin brightness index of other experimental groups. It shows that the ability for increasing rate of skin brightness index of the lotion of the glycerol extract of the dragon fruit flower Is excellent. Detail statistical analysis results of the increasing rates of skin brightness index between the experimental groups are shown in Table 5.

TABLE 5

| Sample | Lotion of butanediol extract | Lotion of glycerol extract | Placebo |
|---|---|---|---|
| Lotion of ethanol extract | 0.012* | 0.002* | 0.015* |
| Lotion of butanediol extract | — | 0.019* | 0.003* |
| Lotion of glycerol extract | — | — | 0.001* |

*a statistical significance between groups (P < 0.05).

Therefore, the extract of the dragon fruit flower prepared by the method for preparing the extract of the dragon fruit flower of the present disclosure has the ferrous ion chelating ability, the DPPH free radical scavenging activity, and the ability for promoting cell proliferation and cell migration of fibroblast cells, so that the extract of the dragon fruit flower can be further used in fabricating drugs for enhancing wound healing. Furthermore, a lotion including the extract of the dragon fruit flower of the present disclosure can improving a long-lasting moisturizing ability and a short-acting moisturizing ability of the skin of the subject and can be further used to decrease the skin melanin index and increase the skin brightness index, so that the extract of the dragon fruit flower has a well potential in the field of aesthetic medicine.

Although the present disclosure has been described in considerable detail with reference to certain embodiments thereof, other embodiments are possible. Therefore, the spirit and scope of the appended claims should not be limited to the description of the embodiments contained herein.

What is claimed is:

1. A method for preparing an extract of a dragon fruit flower, comprising:
   providing the dragon fruit flower;
   drying the dragon fruit flower, and then cutting the dragon fruit flower into chips after drying so as to obtain a plurality of dragon fruit flower pieces;
   performing an extraction process, wherein the extraction process comprises:
   providing a mixing step, wherein an alcohol solution is mixed with the dragon fruit flower pieces so as to form a mixture, and the alcohol solution is a glycerol solution;
   providing a heating step, wherein the mixture is heated up to a heating temperature and then is reacted for a heating time;
   providing a cooling step, wherein the mixture is cooled down to a room temperature and then is rested for a cooling time;
   providing a reheating step, wherein the mixture is heated up to a reheating temperature and then is reacted for a reheating time; and
   providing an extracting step, wherein the mixture is cooled down to the room temperature and then is stirred and reacted for an extracting time, and
   removing a solid component from the mixture so as to obtain an extract liquid, wherein the extract liquid comprises the extract of the dragon fruit flower.

2. The method of claim 1, wherein a volume percent concentration of the glycerol solution ranges from 10% to 50%.

3. The method of claim 2, wherein the volume percent concentration of the glycerol solution ranges from 15% to 40%.

4. The method of claim 1, wherein a weight ratio of the dragon fruit flower pieces to the alcohol solution in the mixing step ranges from 1:1 to 1:10.

5. The method of claim 4, wherein the weight ratio of the dragon fruit flower pieces to the alcohol solution in the mixing step ranges from 1:2 to 1:6.

6. The method of claim 1, wherein the heating temperature ranges from 40° C. to 70° C.

7. The method of claim 6, wherein the heating temperature ranges from 50° C. to 60° C.

8. The method of claim 1, wherein the heating time ranges from 6 hours to 10 hours.

9. The method of claim 8, wherein the heating time is 8 hours.

10. The method of claim 1, wherein the cooling time ranges from 20 hours to 28 hours.

11. The method of claim 10, wherein the cooling time is 24 hours.

12. The method of claim 1, wherein the reheating temperature ranges from 40° C. to 70° C.

13. The method of claim 12, wherein the reheating temperature ranges from 50° C. to 60° C.

14. The method of claim 1, wherein the reheating time ranges from 6 hours to 10 hours.

15. The method of claim 14, wherein the reheating time is 8 hours.

16. The method of claim 1, wherein the extracting time ranges from 5 days to 9 days.

17. The method of claim 16, wherein the extracting time is 7 days.

18. The method of claim 1, wherein the solid component is removed by a centrifugation method, a filtration method, or a combination thereof.

* * * * *